United States Patent [19]

Kambara et al.

[11] Patent Number: 5,290,419
[45] Date of Patent: Mar. 1, 1994

[54] FLUORESCENCE DETECTION TYPE ELECTROPHORESIS APPARATUS

[75] Inventors: Hideki Kambara, Hachiouji; Takashi Anazawa, Kokubunji; Keiichi Nagai, Higashiyamato; Hiroaki Machida, Kodama; Hisanori Nasu, Yokohama, all of Japan

[73] Assignees: Hitachi, Ltd.; Hitachi Electronics Engineering Co., Ltd., both of Tokyo; Hitachi Software Engineering Co., Kanagawa, all of Japan

[21] Appl. No.: 45,135

[22] Filed: Apr. 12, 1993

[30] Foreign Application Priority Data

Apr. 14, 1992 [JP] Japan ................... 4-094568

[51] Int. Cl.⁵ .................. G01N 27/26; G01N 27/447
[52] U.S. Cl. .................... 204/299 R; 204/182.8; 356/344
[58] Field of Search ................ 204/299 R, 182.8; 356/344

[56] References Cited

U.S. PATENT DOCUMENTS 4,832,815 5/1989 Kambara et al. ............. 204/299 R
5,062,942 11/1991 Kambara et al. ............. 204/299 R

FOREIGN PATENT DOCUMENTS 63-231247 9/1968 Japan .
61-044353 5/1986 Japan .
1-116441 5/1989 Japan .
2-203255 8/1990 Japan .
2-269936 11/1990 Japan .
3-020644 1/1991 Japan .
3-082946 4/1991 Japan ....................... 204/299 R
3-293557 12/1991 Japan .

OTHER PUBLICATIONS

Lloyd M. Smith et al "Fluorescence detection in automated DNA sequence analysis" Nature vol. 321 (1986) 674–679.

*Primary Examiner*—John Niebling
*Assistant Examiner*—John S. Starsiak, Jr.
*Attorney, Agent, or Firm*—Antonelli, Terry, Stout & Kraus

[57] ABSTRACT

In the multi-color fluorescence detection type electrophoresis apparatus provided with the electrophoresis gel plate, excitation laser source, means to separate the fluorescence images according to each emission wavelength, and the detector of the fluorescence subjected to wavelength selection, two or more laser sources are provided, each of laser lights is irradiated on the sample on a time-sharing basis, and the filter which cuts off the scattered light of each the laser synchronous with the laser beam is installed in front of the wavelength separation means thereby providing simultaneous, quick and real-time analysis of a great number of samples such as DNA and RNA labeled by many types of fluorophores, without overlapping the wavelengths of the excitation light and the fluorescence.

9 Claims, 3 Drawing Sheets

FLUORESCENCE DETECTION TYPE ELECTROPHORESIS APPARATUS

BACKGROUND OF THE INVENTION

The present invention relates to the electrophoresis separation and photodetection apparatus for the DNA or RNA, especially to the fluorescence detection type electrophoresis apparatus suited to detect the fluorescence having different wavelengths emitted from the samples which are labeled with a plurality of fluorophores.

The gene diagnosis and the analysis of human genome require a quick analysis of many samples. The conventional method used for DNA detection including the base sequence determination for DNA has been autoradiography, whereby the DNA is labeled with the radioactive element, and the pattern of the DNA fragment subjected to electrophoresis gel separation according to its length is photographed and read out. Furthermore, automatic DNA sequencers have recently been developed, whereby the DNA fragment is labeled with the fluorophore to provide real time detection (Nature, Vol. 321, 1986, pp. 674–(679)).

These sequencers use a plurality of fluorophores having different emission wavelengths to distinguish the four types of bases from one another or classifies the types of DNA to be detected. Namely, the means to identify signals emitted from a plurality of fluorophores have been proposed, including;

(1) a system which uses the rotary filter provided with four types of filters which selectively transmit the light emitted from the fluorophores installed on the front of the detector (Nature, Vol. 321, 1986, pp. 674–679), (2) a system which uses the image splitting prism (Japanese Patent Application Laid-open 2-269936 and U.S. Pat. No. 5,062,942), and (3) a system which uses the wavelength dispersion prism (Japanese Patent Application Laid-open 1-116441 and U.S. Pat. No. 4,832,815).

However, the multicolor fluorescence detection system using the rotary filter has a problem; the increased number of fluorophores leads to reduced time to measure each fluorophore, hence reduced sensitivity. The conventional method of using the latter image splitting prism permits identification of about four types of fluorophores excited by one laser. However, effective excitation by one laser is possible up to two types of fluorophores generally; use of more than two types of fluorophores requires two or more excitation light sources in practice. As a result, use of two or more excitation light sources have often caused overlapped bands between the second excitation light wavelength and the fluorescent wavelength excited by the first excitation light. Especially, greater numbers of fluorophores tend to increase the frequency of overlaps between the excitation light wavelength and emission wavelength of the fluorophore disadvantageously in measuring. Namely, one laser is used generally because of the measuring problem. However, in this case, the multicolor fluorescence labeling method which detects the fluorescences with different wavelengths from samples labeled with these plurality of fluorophores has the problem of poor excitation efficiency with respect to some of the fluorophores, and of poor sensitivity in general; this is because of lack of the laser system which ensures effective excitation of all the fluorophores. At present, the apparatus using said method is placed on the market by Applied Biosystems Inc. in the U.S.; it has 24 migration lanes. This apparatus permits one measurement in ten to twelve hours, and allows only twenty-four samples at one time.

Another known method uses the procedure of labeling the DNA by a kind of fluorophores, thereby identifying the terminal species according to the difference of the migration lanes. However, this single-color fluorescence labeling system using one fluorophore label permits one measurement in five to six hours, allowing eight to ten samples at one time; the number of samples measured per day (throughput) is limited to only 16 to 20, when two daily measurements are assumed.

As discussed, the conventional DNA sequencers have been far from satisfactory in ensuring a quick, simultaneous analysis of many samples.

SUMMARY OF THE INVENTION

The object of the present invention is to provide the highly sensitive multi-wavelength separating and detecting means which detects fluorescences, from many fluorophores discriminatingly without reducing the detection sensitivity, thereby solving the problems involved in the conventional methods; to put it more concretely, its object is to provide a real time multicolor fluorescence detection DNA analyzer featuring highly sensitive and excellent throughput, which ensures efficient gene diagnosis and human genome analysis.

To achieve said objective, the fluorescence detection type electrophoresis apparatus according to the present invention has;

i) means for electrophoretically separating a group of samples comprising the samples labeled with a plurality of fluorophores, ii) means for exciting the fluorophores labeling the samples and to cause emission of fluorescence, iii) means for wavelength selection of the fluorescence, iv) means for detecting said fluorescence subjected to wavelength selection;

wherein the exciting means uses two or more excitation lights to irradiate the sample on a time shared basis, and said wavelength selection means is provided with the filter to cut off the scattered light synchronized with the timed-shared irradiation.

The electrophoresis separation means for said group of samples may use the electrophoresis gel plate which is widely known.

To get the two or more excitation lights on a timed shared basis, the exciting means generally comprises two or more laser sources and light chopper (normally, the rotary shutter is used) corresponding to the time sharing.

The scattered light cutoff filter of the wavelength selection means is capable of cutting off the light having the same wavelength as the excitation light. Two or more filters must be synchronized with the time-shared irradiation to ensure that the cutoff wavelength will be the same as that of the scattered light reaching at that time point (namely, excitation light at that time). In this case, if the filter is used which cuts off all the wavelengths of excitation lights at all time points, the fixed filter will do.

Said wavelength selection means has a function of feeding a plurality of emission wavelengths emitted from a plurality of fluorophores to the detecting means, with each light separated from each other according to the wavelength; this requires one of the following provisions;

(a) comprising means for splitting the fluorescent image, and band pass filters having different transmitted wavelength bands in the number corresponding to that of the split images, (b) comprising a wavelength dispersion prism, and (c) comprising a dichroic mirror which separates the light into the transmitted light and reflected light according to the wavelength.

The combination of the image splitting means (e.g., image splitting prism, image splitting lens, image splitting mirror) and band pass filters listed in (a) is described in great detail in the U.S. Pat. No. 5,062,942, and all the image splitting methods described therein are applicable to the present invention. Use of the wavelength dispersion prism given in (b) is described in the U.S. Pat. No. 4,832,851 for the case of the direct vision prism. Needless to say, the normal prism may be used in place of the direct vision prism. Use of the dichroic mirror in (c) is described concretely in the EMBODIMENT.

As discussed above, the present invention can utilize the image splitting method and image dispersion method for the real time multicolor fluorescence detection DNA analyzer illustrated in U.S. Pat. Nos. 5,062,942 and 4,832,851, and can be said to be an extension of these U.S. techniques.

Said excitation means uses two or more laser sources the number of which is limited to six or less. The wavelength band used for measurement is 450 to 700 nm, and the space for maximum emission wavelengths of the fluorophores is about 20 nm. For this reason, at most ten to twelve types of fluorophores can be used for this purpose, and the maximum number of the excitation lasers is about six.

However, some of the excitation laser wavelengths may come around the emission maximum wavelengths of some fluorophores, which result in reducing the number of available fluorophores. This can be overcome by grouping lasers as well as fluorophores such that the lasers and fluorophores in the same group do not interfere each other. Usually two groups are enough for this.

The wavelength turn around time for said excitation light is 0.5 to 3 sec.; about 1 second is often used in general. Insufficient turn around time will reduce sensitivity, while excessive turn around time will reduce measuring accuracy; both cases are undesirable.

The applicable lasers with their wavelengths include the argon laser (488 nm or 515 nm), the YAG laser (532 nm), the He-Ne laser (543 nm, 594 nm or 632 nm) and semiconductor laser (670 nm).

Said scattered light cutoff filter is installed in front of the means for separating the emission light wavelengths emitted from a plurality of fluorophores.

The fluorescence detecting means to be used may be the known one which is an optical area sensor or a plurality of optical line sensors.

Excitation light is conveniently irradiated on the specified position of the electrophoresis gel plate from the side of the gel plate, parallel to the gel plate and perpendicular to the migration path. This will cause the excitation light (laser light) to cross perpendicularly all the migration path at the specified height of the gel plate.

The fluorescence detection type electrophoresis apparatus according to the present invention causes alternate irradiation of two or more excitation lights, and causes the scattered light cutoff filter to operate synchronous therewith (or provides installation of the fixed filter which cuts off all excitation lights), so that the wavelength selection means having a wavelength separation function receives only the fluorescence; it eliminates the interruption of measurement by the scattered excitation light adjacent to the emission wavelength of the fluorophores which is most likely to interfere by turning on or off excitation lights alternately in time, and ensures separation and detection of the wavelength of fluorescence in a short time.

The electrophoresis apparatus according to the present invention has an advantage of exciting each of many fluorophores by the laser optimum to each fluorophore. When the excitation light wavelengths are close, fluorescence and part of the excitation light are overlapped with each other, causing detection failure. In the case of excitation lights where the wavelengths are very close to each other and tend to cause interference in measurement, mutual interference is removed by time sharing. In the case of excitation lights where the wavelengths are very far from each other, the time-shared duty cycle is reduced to a half by simultaneous irradiation, eliminating the possibility of losing much sensitivity. Furthermore, the wavelength dispersion prism, image splitting prism with filter provided with cylindrical lens or tile like is used for wavelength selection, eliminating the possibility of losing the amount of light received by the two-dimensional detector. This provides a great volume of received light and high degree of sensitivity in the multicolor fluorescence detection type DNA detection system which uses a plurality of fluorophores for labeling of DNA and others.

The relationship between wavelengths of the excitation lights, and the relationship between emission wavelengths of fluorophores should preferably be selected as follows:

1) The wavelengths of excitation lights within the group of excitation lights to be irradiated simultaneously are separate from each other 40 nm or more, and excitation lights irradiated alternately are separate from each other 20 nm or more.

2) The maximum emission wavelengths of the fluorophores and the excitation light wavelengths are separate from each other 20 nm or more within the group of fluorophores emitting fluorescence simultaneously. Intentional separation of 20 nm or more is not required for the maximum emission wavelengths of the fluorophores emitting fluorescence alternately.

DESCRIPTION OF PREFERRED EMBODIMENTS

Embodiments of the present invention will be described with reference to figures.

EMBODIMENT 1

Figure 1:
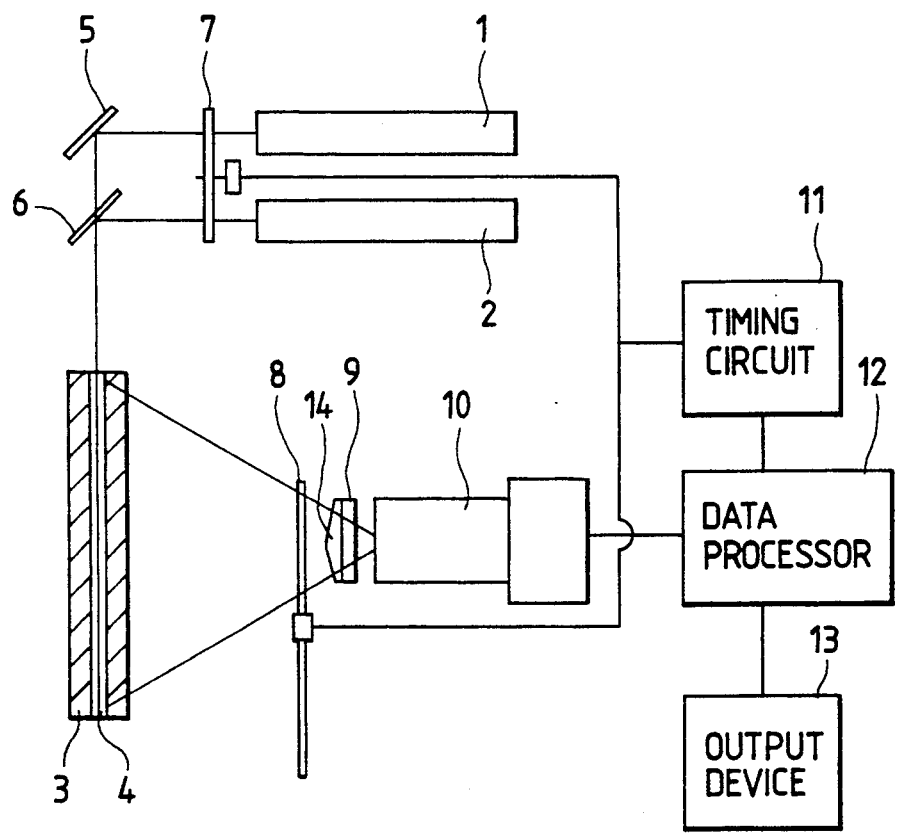
FIG. 1 is a schematic view illustrating the fluorescence detection type electrophoresis apparatus which separates and detects many types of fluorescence labels in one embodiment of the present invention.

FIG. 1 shows the first embodiment of the electrophoresis apparatus according to the present invention. In FIG. 1, the irradiation region, namely the excitation means, comprises laser sources 1 and 2 and rotary shutter 7. The type and number of said laser sources are adequately selected according to the number of the fluorescent signal emitted from nucleic acids. If there are many types of nucleic acids to be detected, the type and number of the laser sources are selected accordingly. When the fluorescent signal for each base is to be specified even in the case of a single nucleic acid, the laser source is selected according to the said type of the base. The fluorophore labeling the probe or the like is selected according to the type of the said laser source. Normally, two fluorophores can be combined for a single laser source. Namely, it is possible to separate and detect the light emitted from the fluorophores having different emission wavelengths which can be excited by said laser light, but it is more effective if wavelengths are separate far from each other in that case.

The method of binding these fluorophores as labeling probes to the polynucleotides is not limited in any way. For example, it is possible to use the method of using the amino group introducing reagent to provide direct fluorescence label to the nucleic acid base or the method mentioned in Japanese Patent Application Laid-open 61-44353; namely, it is possible to use the method of replacing the phosphate bonding of the fluorescence labeling region of the polynucleotide with the phosphonium bonding having the functional group to realize the fluorescence labeling by fluorescence bonding of this functional group, thereby introducing the label into any desired region of the polynucleotide.

FIG. 1 shows the case of labeling DNA fragments by four types of fluorophores and detecting them using two light sources. In this case, for example, it is preferred to use FITC (fluorescein isothiocyanate having an excitation wavelength of 490 nm and emission wavelength of 520 nm), dichloro FITC (having an excitation wavelength of 515 nm and emission wavelength of 534 nm), TRITC (Tetramethylrhodamine isothiocyanate having an excitation wavelength of 550 nm and emission wavelength of 578 nm), and sulforhodamine 101 (Texas Red TM manufactured by Molecular Probe Inc., having an excitation wavelength of 594 nm and emission wavelength of 615 nm), as labeling fluorophore; for example, Ar ion laser (488 nm) may preferably be used as the excitation light source (laser 1) of the FITC and dichloro FITC, and argon ion laser (515 nm), YAG laser (532 nm), and He-Ne (543 nm) laser may preferably be used as the excitation light source (laser 2) of the TRITC and sulforhodamine 101. In the present embodiment, laser 1 uses the argon ion laser (having a wavelength of 488 nm), while laser 2 uses the YAG laser (having a wavelength of 532 nm).

Two lasers 1 and 2 alternately selected by rotary shutter 7 or light switch at specified intervals, and two lasers 1 and 2 irradiate the separation gel 4 of the electrophoresis gel plate 3 alternately in a linear form from the side of the separation gel 4 perpendicularly to the direction in which the DNA fragments migrate. Laser beams from the lasers 1 and 2 are reflected by full-reflection mirror 5 and dichroic mirror 6, respectively (dichroic mirror 6 reflects the laser light from laser 2 having a wavelength of 532 nm (incident angle of 45 deg.) transmitting others), resulting in linear irradiation on the separation gel 4. The turn around time for rotary shutter 7 is about one second.

When four types of fluorophores are made to correspond to four bases (A: adenine, C: cytosine, G: guanine, T: thymine) of the DNA, the optical axes of laser 1 and laser 2 must be made agree to each other to provide a linear irradiation on the same position of the separation gel 4. When four types of the DNAs to be analyzed by the four types of fluorophores are to be identified, the optical axes of laser 1 and laser 2 need not necessarily be made to agree to each other.

Figure 2A:
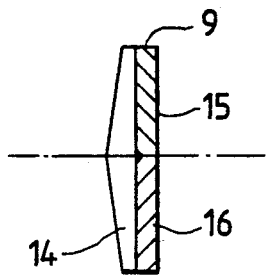
FIG. 2a is a sectional view representing the filter with image splitting prism used in the fluorescence detection type electrophoresis apparatus in one embodiment of the present invention.

In FIG. 1, the wavelength selection region comprises rotary colored glass filter 8 and the image splitting prism with filter which comprises image splitting prism 14 splitting the image into two and multi-band pass filter 9. Rotary colored glass filter 8 has a rotary plate provided with a colored glass filter which is designed to cut off the scattered light having the same wavelength as that of the excitation laser emitted from the laser irradiation region, and rotates synchronously with the movement of the shutter 7 or optical switch for alternate selection between laser 1 and laser 2 employed for irradiating the separation gel 4 alternately. That is, only the fluorescence emitted during the excitation by each laser, passes through this rotary colored glass filter 8 and scattered light cannot pass through. Needless to say, rotary colored glass filter 8 may be replaced by a vertical or horizontal shift type selector filter. The prism 14 splitting the image into two is installed (splitting prism to split images into three parts when three fluorophores are excited by one laser) in front of the image forming lens (not illustrated) installed in front of the two-dimensional detector to form two fluorescent images on the two-dimensional detector surface. FIG. 2a illustrates the sectional view of one embodiment for the image splitting prism with filter which comprises image splitting prism 14 splitting the image into two and multi-band pass filter 9 which can pass fluorescence from multiple fluorophores. Multi-band pass filter 9 is mounted on two surfaces of image splitting prism 14 from which light exits. The constituents of multi-band pass filter 9 are determined by the combination of the laser sources to be used and the fluorophores. In the present embodiment, for example, multi-band pass filter 9 can comprise band pass filter 15 (transmission band; 535 to 590 nm) and band cutoff filter 16 (cut-off wavelength band; 525 to 600 nm). Namely, band pass filter 15 allows passage of the fluorescences from dichloro FITC and TRITC, while band cutoff filter 16 allows passage of the fluorescence from FITC and sulforhodamine 101. The band pass filter 15 and band cutoff filter 16 generally uses the multilayer dielectric filter or a combination of multilayer dielectric filter with the colored glass filter.

Figure 2B:
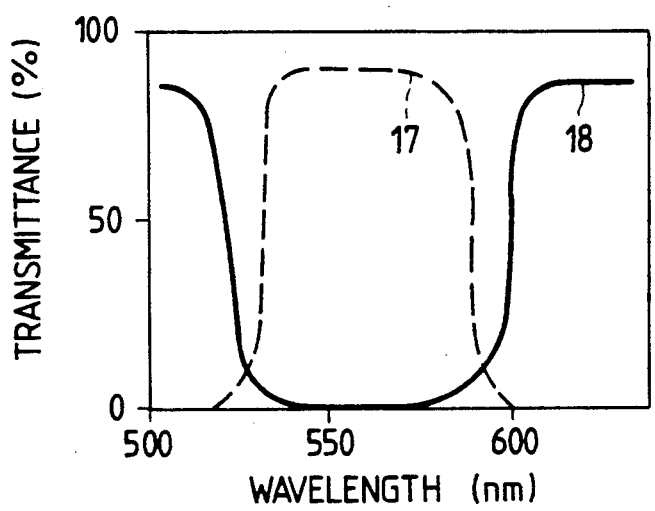
FIG. 2b is a graph showing the transmission spectrum of the multi-band pass filter used in one embodiment of the present invention.

FIG. 2b illustrates the transmission spectrum of multi-band pass filter 9, namely, band pass filter 15 and band cutoff filter 16. In the wavelength region of the transmission band of the band pass filter 15 where the transmittance at the transmission spectrum 17 is great, the transmittance of band cutoff filter 16 is practically zero (reflection rate 100 percent), while in the wavelength region of the reflection (cutoff) band of the band pass filter 15 where the transmission spectrum is practically zero, the transmittance of the band cutoff filter 16 is great and the band cutoff filter 16 functions as a band pass filter. That is, of these two filters 15 (A) and 16 (B), A acts as a reflection (cutoff) filter and B as a transmission filter in the specific wavelength band; and in another wavelength region, B acts as a reflection (cutoff) filter and A as a transmission filter. Two filters 15 (A) and 16 (B) acts as a band pass filter and band reflection filter complementary thereto. During irradiation of laser 1 the fluorescent images from the FITC and dichloro FITC are detected via the detector to be described below, whereas during irradiation of laser 2 the fluorescent images from the TRITC and sulforhodamine 101 in place of said fluorescences are detected.

It should be noted that, although rotary filter 8 to eliminate the scattered light is provided in the present embodiment, it is also possible to use a solid filter comprising the overlapped combination of the colored glass filter to cut off the scattered light of one laser and the narrow band reflection filter to cut the scattered light of the other laser.

Furthermore, it is also possible to install a separate cylindrical lens to increase the photodetecting capacity of said detector as disclosed, for example, in the U.S. Pat. No. 5,062,942, col. 4, line 33 to col. 5, line 9 or in Japanese Patent Application Laid-open 3-20644.

In addition, the wavelength dispersion prism can also be used as a wavelength selection means, where it is preferred to use the prism made of SF glass having a small $\nu d$ value and a great refractive index nd value. The $\nu d$ value is a dispersion of the refractive index of D-line and is expressed by equation $(nd-1)/(nf-nc)$. The nd, nf and nc represent the refractive indices of the wavelength of the D-line (587.8 nm), wavelength of the F-line (481.6 nm) and wavelength of the C-line (656.3 nm), respectively. Said prism is installed in the direction where the wavelength dispersion is intended in the direction different from the direction of the formed fluorescent image line, in place of image splitting prism 14 and multi-band pass filter 9 shown in FIG. 1. For example, when the photo-linesensor is to be used as a two-dimensional detector to be described later, said prism is normally installed parallel to electrophoresis gel plate 3 in front of the region subjected to linear laser irradiation in order to cause wavelength dispersion perpendicular to the linear fluorescent image (linear image). In this case also, a scattered light cutoff means such as rotary colored glass filter must be used to permit the two-dimensional detector to accept only the fluorescence.

In FIG. 1, the detector comprises two-dimensional detector 10 sensing the selected fluorescences, timing circuit 11, data processor 12 and output device 13. The fluorescence in the distinguished state at said detector is detected by the photodetecting element of two-dimensional detector 10. Said detector can be either a plurality of photo-linesensor or photo-areasensor. In the present embodiment, use of the photo-areasensor is preferred for handling ease. Reading of the signal issued from the two-dimensional detector 10 is controlled by timing circuit 11, and is processed by data processor 12, to be output by the output device 13.

EMBODIMENT 2

Figure 3:
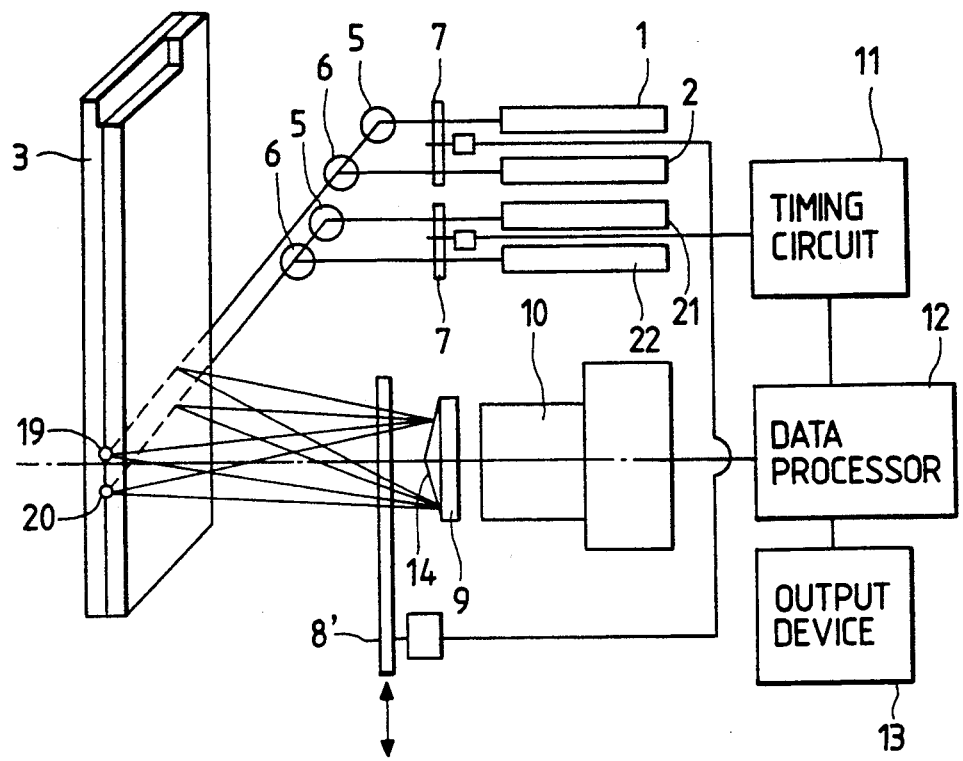
FIG. 3 is a schematic view illustrating the fluorescence detection type electrophoresis apparatus which separates and detects eight types of fluorescence labels in another embodiment of the present invention.

FIG. 3 represents the second embodiment of the electrophoresis apparatus according to the present invention. Said electrophoresis apparatus is the fluorescence detection type electrophoresis apparatus to separate and detect the object labeled by eight types of fluorophores.

In FIG. 3, the irradiation region is comprised of laser sources 1, 2, 21 and 22 and rotary shutter 7. The criteria for selection of the laser sources and the corresponding fluorophores are the same as described for EMBODIMENT 1. For example, argon ion laser (wavelength of 488 nm) 1, green He-Ne laser (543 nm) 2, yellow He-Ne laser (594 nm) 21, and red He-Ne laser (633 nm) 22 are used as lasers; and as their corresponding fluorophores, succinyl fluorescein (SF505: emission wavelength 508 nm) and dichloro FITC (emission wavelength of 535 nm) for 1; TRITC (wavelength of 575 nm) and sulforhodamine (isomer of the Texas Red TM, having an emission wavelength of 596 nm) for 2; sulforhodamine 101 (Texas Red TM, having an emission wavelength of 615 nm) and HR-II (rhodamine fluorophore, manufactured by Molecular Probs, Inc.: having an emission wavelength of 635 nm) for 21; and Ultralite 660 TM (manufactured by Ultra, Diagnostic, Inc., having an emission wavelength of 657 nm) and Ultralite 680 TM (manufactured by Ultra, Diagnostic, Inc., having an emission wavelength of 682 nm) for 22.

In said cases, laser sources must be laid out to ensure that laser light from laser source 1 and laser light from laser source 2 will be located on the same optical axis, and laser light from laser source 21 and laser light from laser source 22 will be also located on the same optical axis. The distance between said axes can be adjusted accounting the distance between two images separated with the splitting prism. The direction of laser irradiation is the same as described in EMBODIMENT 3. Laser 1 and laser 21 irradiate the gel plate simultaneously, and laser 2 and laser 22 irradiate it simultaneously at specified time intervals. The alternative irradiation of the lasers is controlled by rotary shutter 7 at specified time intervals; the turn around time for rotary shutter 7 is about every one second.

In FIG. 3, the wavelength selection region comprises shift type colored glass filter 8', image splitting prism 14 and multi-band pass filter 9. To be more concrete, each fluorescence issued from each of the regions 19 and 20 irradiated by the laser lights from the above two groups is made into parallel in the vertical direction by the cylindrical lens (not illustrated), then it passes through the shift type colored glass filter 8', which is a scattered light cutoff filter comprising the shift type selection filter. This filter 8' changes into two filters synchronous with irradiation by two groups of lasers as shown in EMBODIMENT 1. Each filter is composed of two colored glass filters spliced on the top and bottom, and light from the top irradiation region and light from the bottom irradiation region go into the top and bottom filters, respectively. The light having passed through the filter 8' passes through the cylindrical concave lens (not illustrated), then through the image splitting prism 14 and multi-band pass filter 9. Thereafter the light is converged on the photodetecting element of two-dimensional detector 10 as four fluorescent linear images by the image forming lens (not illustrated). The signal obtained on the photodetecting element of two-dimensional detector 10 is read synchronously with the laser irradiation light, as shown in EMBODIMENT 1.

The prism can be used as wavelength dispersion means as in EMBODIMENT 1. The characteristics of two band pass filters constituting multi-band pass filter 9 are similar to the relationship between the band pass filter and band cut-off (reflection) filter, as shown in EMBODIMENT 1. Namely, when using the lasers and fluorophores exemplified above, the first filter has a transmission band in the region of 525 to 580 nm and 625 to 670 nm, while this region for the second filter is a reflection band; the second filter has a transmission band in 490 to 520 nm, 580 to 620 nm and 670 nm or more. The first filter transmits the fluorescence emitted from fluorophores such as dichloro FITC, TRITC, HR-II and Ultralite 660 TM, while the second filter transmits the fluorescence emitted from fluorophores such as SF505, sulforhodamine, Texas Red and Ultralite 680 TM. It alternately reads out four fluorescent linear image signals synchronously with laser irradiation light at specified intervals, thereby obtaining a total of eight types of information of the fluorescent linear image. The constitution and functions of the detector are the same as shown in EMBODIMENT 1.

EMBODIMENT 3

Figure 4:
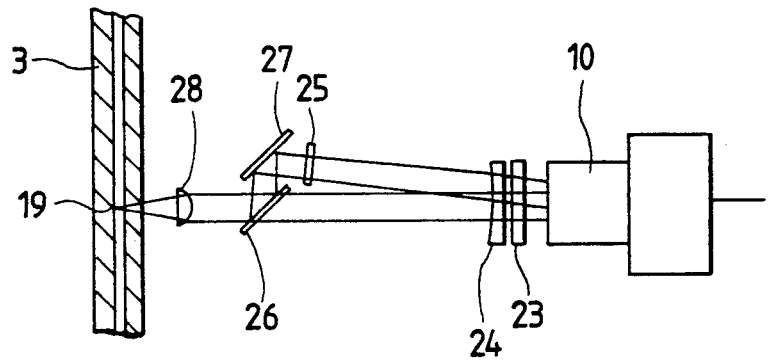
FIG. 4 is a schematic view illustrating the fluorescence detection type electrophoresis apparatus which separates and detects four types of fluorescence labels using the dichroic mirror in still another embodiment of the present invention.

FIG. 4 shows the constitution of the wavelength selection region of the fluorescence detection type electrophoresis apparatus in the third embodiment of the present invention which separates and detects the four types of fluorescence labels, using the dichroic mirror. The present embodiment illustrates an example of detecting four types of fluorescence labels. An irradiation region can be prepared according to the type and number of the laser sources and the samples intended for detection, as shown in said Embodiments 1 and 2, to thereby become possible to detect eight or more fluorescence labels. In the present Embodiment, in place of using the image splitting prism, fluorescence liner image reflected by the dichroic mirror 26 is formed on the photodetecting element of two-dimensional detector 10, at the position different from that of the transmitted light of the dichroic mirror 26. The dichroic mirror 26 reflects the light having a specified wavelength band and transmits the light having another band. The dichroic mirror used in the present invention has two or more transmission bands. The light emitted from region 19 exposed to laser irradiation is made into parallel lights in the vertical direction by the cylindrical lens 28, and is then transmitted into the colored glass filter (not illustrated), which is a scattered light cutoff filter comprising the selection filter. Then the light is divided in two directions, using the dichroic mirror 26 which reflects light having one of the fluorescent wavelengths an an angle of 45 deg. Thus, the light reflected by dichroic mirror 26 passes through the full-reflection mirror 27 and through focal distance adjusting lens 25, and enters cylindrical lens 24 which is an image forming lens, multi-band pass filter 23 and two-dimensional detector 10, where it is detected. The light transmitted from dichroic mirror 26 straightly enters cylindrical lens 24 which is used to adjust the perpendicular focal point to the horizontal focal point and to make a fluorescence image on the detector. Two fluorescence line images are formed on the photodetecting element of two-dimensional detector 10 so that the detection becomes possible; each image can also be formed on two separate line sensors.

The fluorescence detection apparatus shown in the said Embodiments has enabled detection of the DNAs on the real time basis using four or more fluorophores at almost the same or higher sensitivity as that of the conventional one-color method. In the electrophoresis apparatus according to the present invention the fluorescence detection apparatus ensures 32 to 40 migration lanes, and time required in one measurement is five to six hours as in the conventional systems. This means that daily throughput has increased from the conventional 24 to 160, registering a jump of 7 times.

It should be noted that, in the figures mentioned above, the same number represents the same parts.

As will be clear from the above description, the fluorescence detection type electrophoresis apparatus according to the present invention provides an efficient, highly sensitive detection of groups of DNA fragments labeled by a great number of labels on the real time basis.

What is claimed is:

1. In the electrophoresis apparatus comprising
   i) means for electrophoretically separating a group of samples composed of the samples labeled by a plurality types of fluorophores,
   ii) excitation means for exciting the fluorophores labeling said samples and emitting fluorescence,
   iii) means for selecting wavelength of said fluorescence, and
   iv) means for detecting said fluorescence subjected to wavelength selection;

a fluorescence detection type electrophoresis apparatus characterized in that said excitation means provides time-shared irradiation of the samples by a plurality of excitation lights, and said means for selecting wavelength has scattered light cut off filters synchronous with the time-shared irradiation of said plurality of excitation lights.

2. A fluorescence detection type electrophoresis apparatus according to claim 1 wherein said scattered light cutoff filter is changed with the light source change to cut the excitation light reaching said filter.

3. A fluorescence detection type electrophoresis apparatus according to claim 2 wherein said means for selecting wavelength is provided with the fluorescence image splitting means and band pass filters in the same number as that of the split images, where, at least, one of the filters has two or more different transmission bands.

4. A fluorescence detection type electrophoresis apparatus according to claim 2 wherein said means for selecting wavelength is provided with a wavelength dispersion prism.

5. A fluorescence detection type electrophoresis apparatus according to claim 2 wherein said means for selecting wavelength is provided with a dichroic mirror having a plurality of transmission bands.

6. A fluorescence detection type electrophoresis apparatus according to claim 2 wherein said means for electrophoretically separating a group of samples is gel electrophoresis.

7. A fluorescence detection type electrophoresis apparatus according to claim 1 wherein said scattered light cutoff filters are installed on the front of the means which separates fluorescences according to each wavelength.

8. A fluorescence detection type electrophoresis apparatus according to claim 1 wherein each of said plurality of excitation lights excites two types of fluorophores.

9. A fluorescence detection type electrophoresis apparatus according to claim 1 wherein said means for detecting said fluorescence is composed of photo-line-sensors or photo-areasensors.

* * * * *